United States Patent
Castro

(10) Patent No.: US 11,012,550 B1
(45) Date of Patent: May 18, 2021

(54) SMART PHONE CASE HAVING INTEGRATED UV LIGHTS

(71) Applicant: John Castro, Palm Bay, FL (US)

(72) Inventor: John Castro, Palm Bay, FL (US)

( * ) Notice: Subject to any disclaimer, the term of this patent is extended or adjusted under 35 U.S.C. 154(b) by 90 days.

(21) Appl. No.: 16/595,574

(22) Filed: Oct. 8, 2019

(51) Int. Cl.
| | |
|---|---|
| *H04M 1/724* | (2021.01) |
| *H04M 1/72409* | (2021.01) |
| *A61L 2/10* | (2006.01) |
| *H05K 5/02* | (2006.01) |
| *H04M 1/21* | (2006.01) |

(52) U.S. Cl.
CPC ......... *H04M 1/72409* (2021.01); *A61L 2/10* (2013.01); *H04M 1/21* (2013.01); *H05K 5/0247* (2013.01); *A61L 2202/11* (2013.01); *A61L 2202/14* (2013.01)

(58) Field of Classification Search
CPC .... H04M 1/72409; H04M 1/21; H04M 1/185; H05K 5/0247; H05K 5/0017; H05K 5/0086; A61L 2/10; A61L 2202/11; A61L 2202/14; H04W 4/80; H04W 76/10
USPC ...................................... 455/550.1
See application file for complete search history.

(56) References Cited

U.S. PATENT DOCUMENTS

| | | |
|---|---|---|
| 8,428,644 B1 | 4/2013 | Harooni |
| D765,633 S | 9/2016 | Northrup |
| 9,442,346 B2 | 9/2016 | Gantz |
| 9,925,390 B2 | 3/2018 | Yehezkel |
| 2011/0195753 A1 | 8/2011 | Mock |
| 2012/0302294 A1 | 11/2012 | Hammond |
| 2016/0089457 A1* | 3/2016 | Liao ................... G06F 1/1686 250/504 R |

* cited by examiner

*Primary Examiner* — Shaima Q Aminzay
(74) *Attorney, Agent, or Firm* — Kyle A. Fletcher, Esq.

(57) ABSTRACT

The smartphone case with integrated UV lights is a lantern. The smartphone case with integrated UV lights comprises a PDD shell, a personal data device, and a UV lamp circuit. The PDD shell contains the personal data device and the UV lamp circuit. The personal data device forms an electrical connection with the UV lamp circuit. The personal data device provides electrical power to the UV lamp circuit. The personal data device controls the operation of the UV lamp circuit. The UV lamp circuit generates an illumination of electromagnetic radiation in the ultraviolet spectrum. The field of illumination of electromagnetic radiation in the ultraviolet spectrum generated by the smartphone case with integrated UV lights detects biological material that is not otherwise illuminated by electromagnetic radiation in the visible spectrum.

20 Claims, 5 Drawing Sheets

SMART PHONE CASE HAVING INTEGRATED UV LIGHTS

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of smartphones and apparatuses for sterilizing objects, more specifically, a method using ultraviolet radiation. (A61L2/10)

SUMMARY OF INVENTION

The smartphone case with integrated UV lights is a lantern. The smartphone case with integrated UV lights comprises a PDD shell, a personal data device, and a UV lamp circuit. The PDD shell contains the personal data device and the UV lamp circuit. The personal data device forms an electrical connection with the UV lamp circuit. The personal data device provides electrical power to the UV lamp circuit. The personal data device controls the operation of the UV lamp circuit. The UV lamp circuit generates an illumination of electromagnetic radiation in the ultraviolet spectrum. the field of illumination of electromagnetic radiation in the ultraviolet spectrum generated by the smartphone case with integrated UV lights detects biological material that is not otherwise illuminated by electromagnetic radiation in the visible spectrum.

These together with additional objects, features and advantages of the smartphone case with integrated UV lights will be readily apparent to those of ordinary skill in the art upon reading the following detailed description of the presently preferred, but nonetheless illustrative, embodiments when taken in conjunction with the accompanying drawings.

In this respect, before explaining the current embodiments of the smartphone case with integrated UV lights in detail, it is to be understood that the smartphone case with integrated UV lights is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the smartphone case with integrated UV lights.

It is therefore important that the claims be regarded as including such equivalent construction insofar as they do not depart from the spirit and scope of the smartphone case with integrated UV lights. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
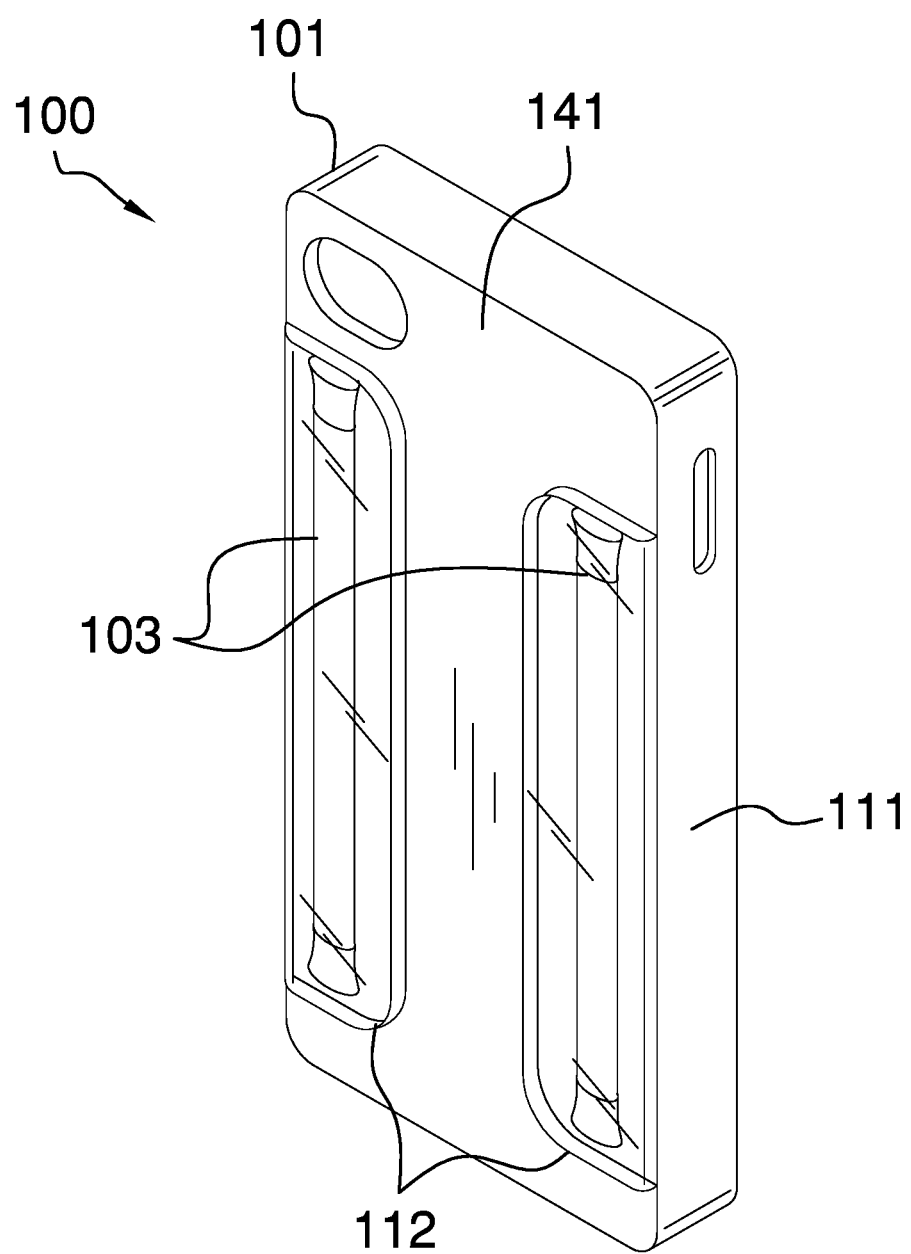
FIG. 1 is a perspective view of an embodiment of the disclosure.
Figure 2:
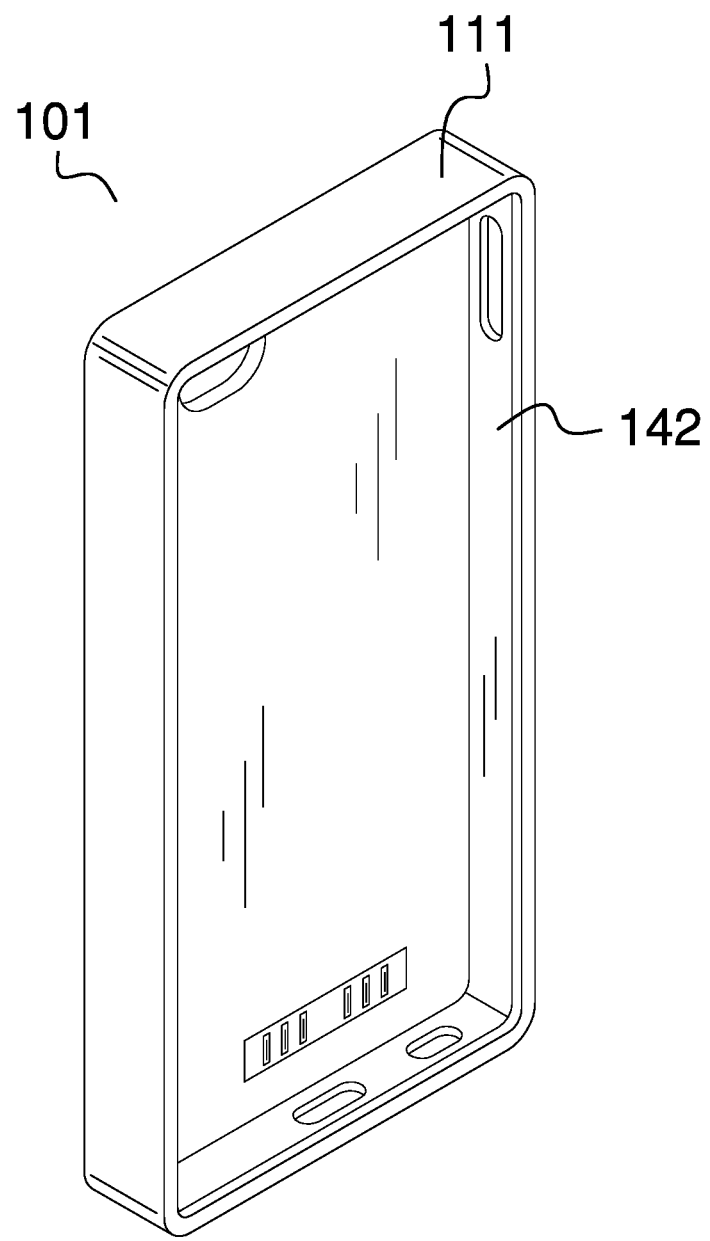
FIG. 2 is a reverse perspective view of an embodiment of the disclosure.
Figure 4:
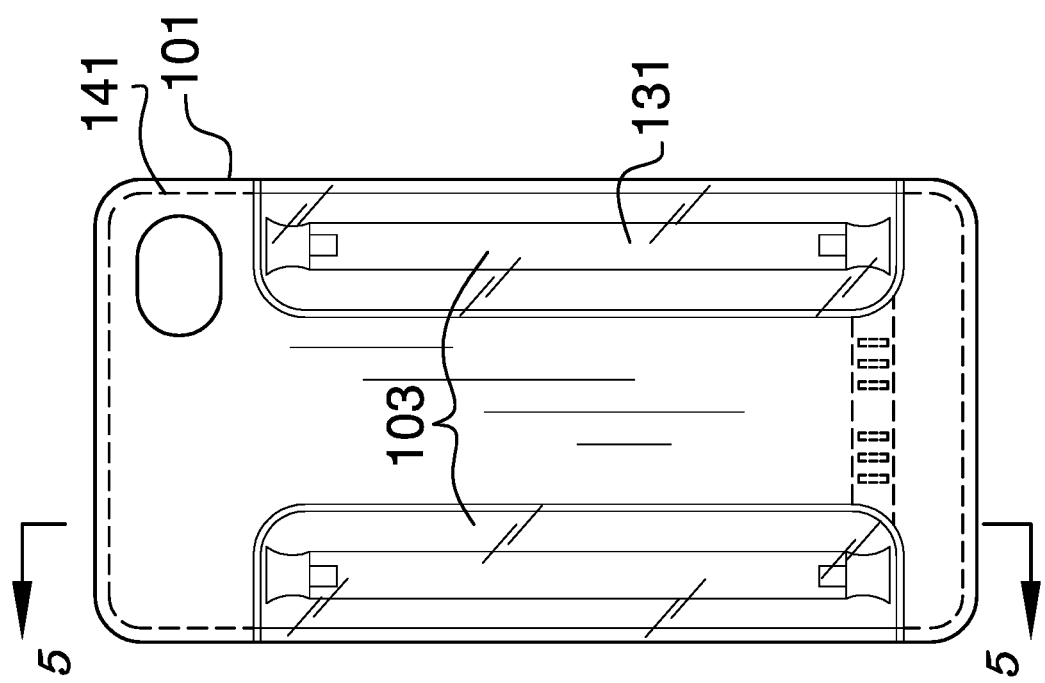
FIG. 4 is a rear view of an embodiment of the disclosure.
Figure 3:
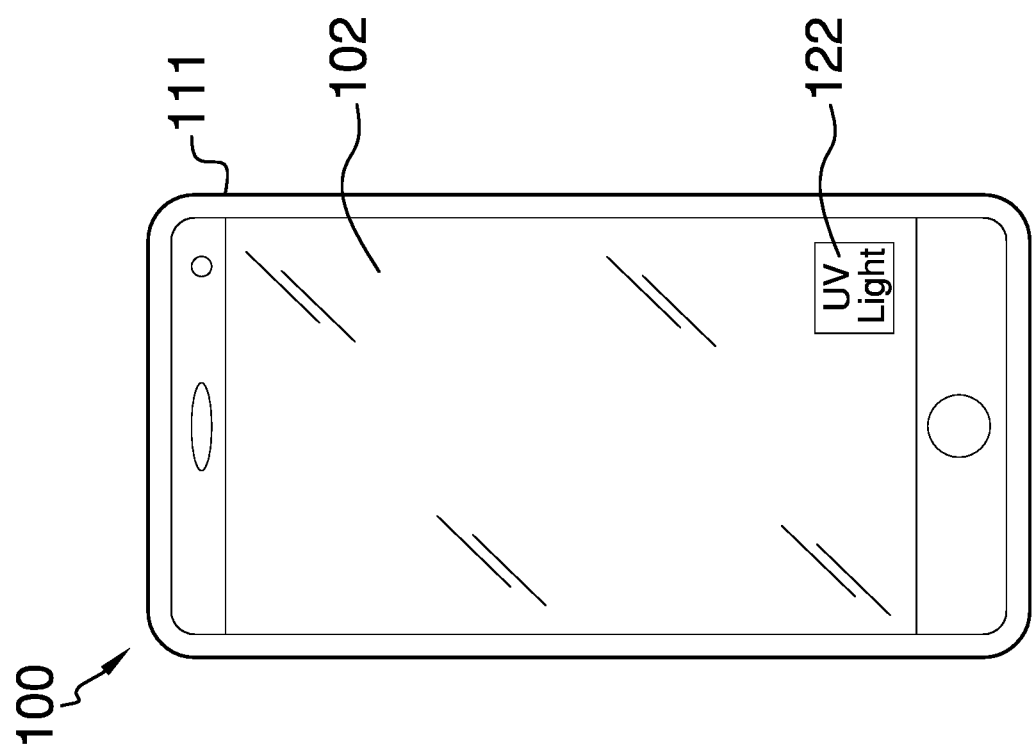
FIG. 3 is a front view of an embodiment of the disclosure.
Figure 5:
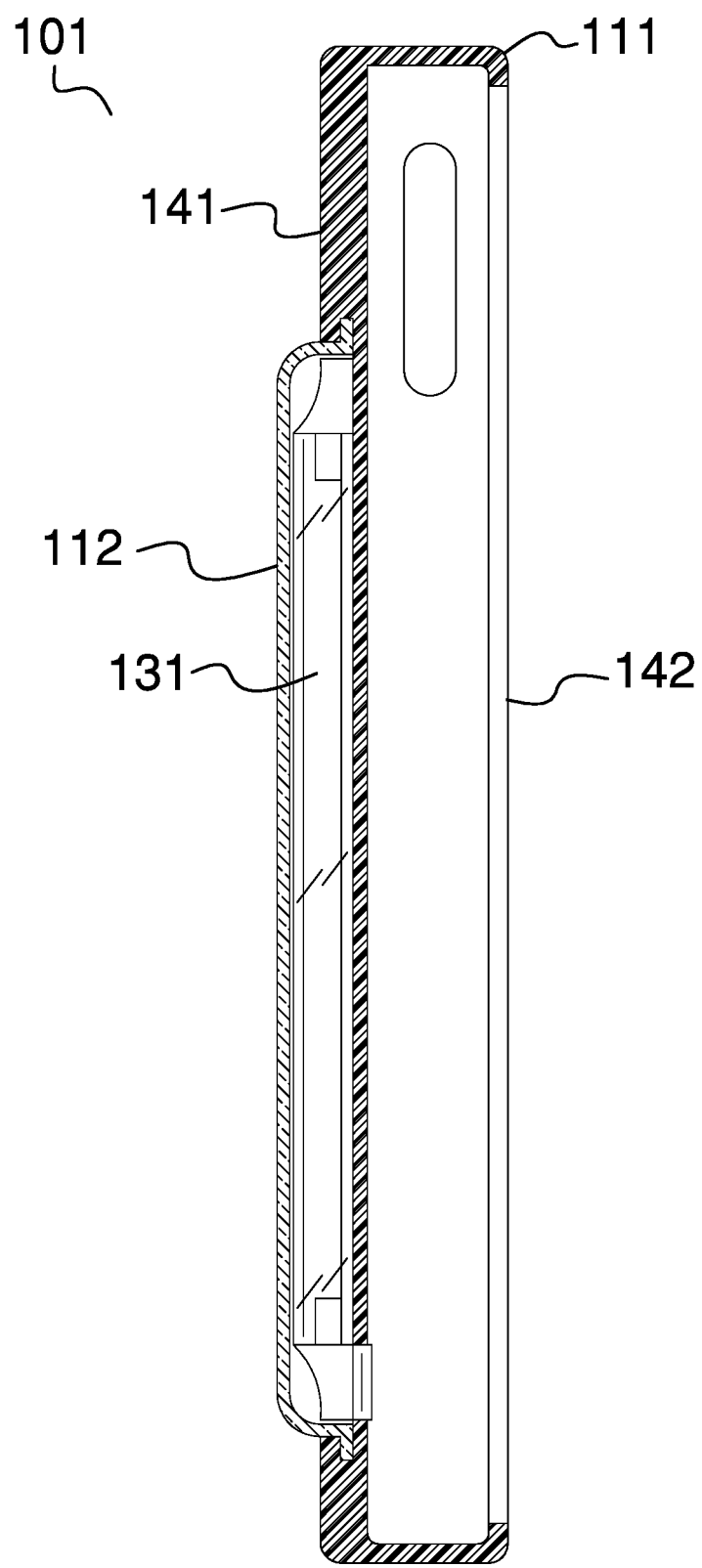
FIG. 5 is a cross-sectional view of an embodiment of the disclosure across 5-5 as shown in FIG. 4.
Figure 6:
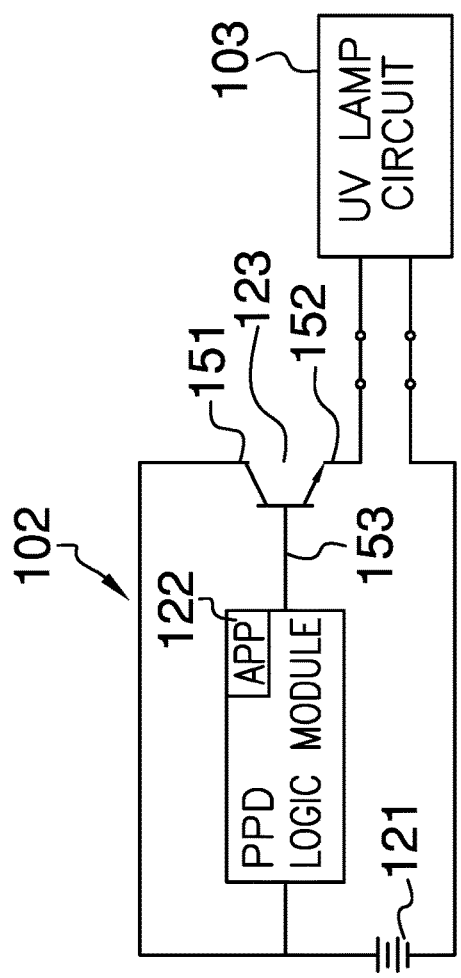
FIG. 6 is a schematic view of an embodiment of the disclosure.
Figure 8:
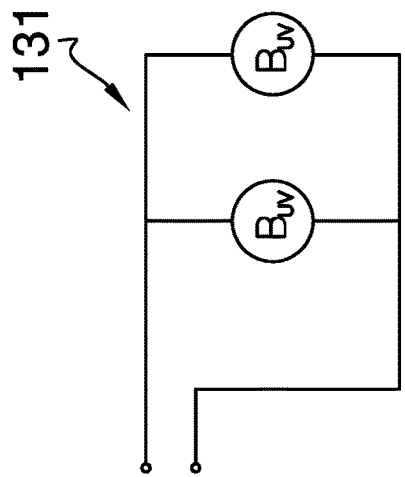
FIG. 8 is a schematic view of an embodiment of the disclosure.
Figure 7:
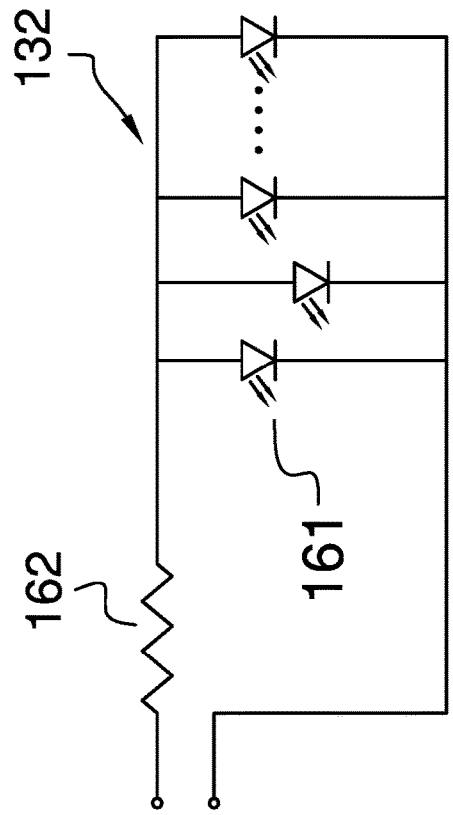
FIG. 7 is a schematic view of an embodiment of the disclosure.

Detailed reference will now be made to one or more potential embodiments of the disclosure, which are illustrated in FIGS. 1 through 8.

The smartphone case with integrated UV lights 100 (hereinafter invention) is a lantern. The invention 100 comprises a PDD shell 101, a personal data device 102, and a UV lamp circuit 103. The PDD shell 101 contains the personal data device 102 and the UV lamp circuit 103. The personal data device 102 forms an electrical connection with the UV lamp circuit 103. The personal data device 102 provides electrical power to the UV lamp circuit 103. The personal data device 102 controls the operation of the UV lamp circuit 103. The UV lamp circuit 103 generates an illumination of electromagnetic radiation in the ultraviolet spectrum. The field of illumination of electromagnetic radiation in the ultraviolet spectrum generated by the invention 100 detects biological material that is not otherwise illuminated by electromagnetic radiation in the visible spectrum.

The PDD shell 101 is a rigid structure. The PDD shell 101 is a protective structure. The PDD shell 101 is formed as a pan. The PDD shell 101 contains the personal data device 102 and the UV lamp circuit 103. The PDD shell 101 is formed with all apertures and form factors necessary to allow the PDD shell 101 to accommodate the use and operation of the personal data device 102 and the UV lamp circuit 103. The PDD shell 101 contains the personal data device 102 such that the personal data device 102 can be used while contained in the PDD shell 101. The PDD shell 101 is a sacrificial structure that protects the personal data device 102 from impact damage. The PDD shell 101 contains the UV lamp circuit 103 such that the field of illumination generated by the UV lamp circuit 103 is targeted in a direction away from the personal data device 102.

Methods to form a PDD shell 101 suitable for the purposes described in this disclosure are well-known and documented in the mechanical arts.

The PDD shell 101 comprises a PDD pan 111 and one or more lamp cavities 112.

The PDD pan 111 is a rigid structure. The PDD pan 111 is a pan shaped structure. The PDD pan 111 is a disk structure. The PDD pan 111 is a sacrificial structure. The PDD pan 111 is sized to receive the personal data device 102. The PDD pan 111 forms a protective shell around the personal data device 102 that protects the personal data device 102 from impact damage. The PDD pan 111 further contains the UV lamp circuit 103. The PDD pan 111 further comprises an open face 141 and a closed face 142.

The open face 141 refers to the open surface of the pan structure of the PDD pan 111. The open face 141 forms a congruent end of the disk structure of the disk structure of the PDD pan 111. The closed face 142 is a congruent end of the disk structure of the disk structure of the PDD pan 111. The closed face 142 is the face of the PDD pan 111 that is distal from the open face 141. The closed face 142 forms a solid surface that protects the personal data device 102 from impact damage.

Each of the one or more lamp cavities 112 is a negative space that is formed in the closed face 142 of the pan structure of the PDD pan 111 of the PDD shell 101. The UV lamp circuit 103 mounts in the one or more lamp cavities 112 such that the UV lamp circuit 103 projects a field of ultraviolet illumination that projects away from the closed face 142 of the PDD pan 111 in a direction away from the personal data device 102.

The personal data device 102 is a programmable electrical device that provides data management and communication services through one or more functions referred to as an application 122. The personal data device 102 further comprises a battery 121, an application 122, and a transistor 123.

The battery 121 is an electrochemical device. The battery 121 converts chemical potential energy into the electrical energy used to power the personal data device 102 and the UV lamp circuit 103.

The transistor is a three-terminal semiconductor device. The transistor 123 operates as switch. The transistor 123 further comprises a collector 151, an emitter 152, and a base 153. The collector 151 is defined elsewhere in this disclosure. The emitter 152 is defined elsewhere in this disclosure. The base 153 is defined elsewhere in this disclosure. The collector 151 and the emitter 152 electrically connect in series between the battery 121 and the lamp circuit 103 such that the transistor 123 controls the flow of electricity into the UV lamp circuit 103. When a voltage is applied to the base 153, current will flow into the base 153 and the transistor 123 will act like a closed switch allowing current to flow from the collector 151 to the emitter 152. When the voltage is removed from the base 153, the transistor 123 will act like an open switch disrupting current flow from the collector 151 to the emitter 152.

The application 122 is a set of logical operating instructions that are performed by the personal data device 102. The addition of an application 122 will provide increased functionality for the personal data device 102. This disclosure assumes that an application 122 exists for the purpose of interacting with the invention 100. Methods to design and implement an application 122 on a personal data device 102 are well known and documented in the electrical arts. The personal data device 102 controls the operation of the UV lamp circuit 103.

The application 122 forms an interface used to control the operation of the UV lamp circuit 103. The application 122 receives instruction through the user interface of the personal data device 102 to illuminate the UV lamp circuit 103. The application 122 instructs the personal data device 102 to apply a voltage to the base 153 of the transistor 123 such that electricity will flow from the battery 121 to the UV lamp circuit 103 to illuminate the UV lamp circuit 103. The application 122 further receives and transmits instructions to extinguish the UV lamp circuit 103 to the personal data device 102.

The UV lamp circuit 103 is an electric circuit. The UV lamp circuit 103 electrically connects to the personal data device 102. The personal data device 102 powers the operation of the UV lamp circuit 103. The personal data device 102 controls the operation of the UV lamp circuit 103. The UV lamp circuit 103 electrically connects in series with the transistor 123 of the personal data device 102. The UV lamp circuit 103 is selected from the group consisting of one or more UV bulbs 131 and a LED circuit 132.

Each of the one or more UV bulbs 131 is a commercially available light bulb. Each of the one or more UV bulbs 131 generates an ultraviolet illumination. Each of the one or more UV bulbs 131 is electrically powered. Each of the one or more UV bulbs 131 is wired in series between the transistor 123 and the battery 121. Each of the one or more UV bulbs 131 are wired in parallel to each other.

The LED circuit 132 generates an ultraviolet illumination. The LED circuit 132 is electrically powered. The LED circuit 132 is wired in series between the transistor 123 and the battery 121. The LED circuit 132 further comprises one or more LEDs 161 and a limit resistor 162.

Each of the one or more LEDs 161 is a two terminal semiconductor device. Each of the one or more LEDs 161 generates electromagnetic radiation when electricity passes through the any selected LED. Each of the one or more LEDs 161 is selected such that each of the one or more LEDs 161 generates electromagnetic radiation in the ultraviolet spectrum. Each of the one or more LEDs 161 mounts in the one or more lamp cavities 112 such that the electromagnetic radiation generated by the one or more LEDs 161 creates the previously described field of illumination. In the first potential embodiment of the disclosure, each of the one or more LEDs 161 are wired in parallel across from each other.

The limit resistor 162 connects in series between the transistor 123 of the personal data device 102 and each of the one or more LEDs 161. The limit resistor 162 limits the flow of electricity through each of the one or more LEDs 161. The limit resistor 162 is defined elsewhere in this disclosure.

The following definitions were used in this disclosure:

Battery: As used in this disclosure, a battery is a chemical device consisting of one or more cells, in which chemical energy is converted into electricity and used as a source of power. Batteries are commonly defined with a positive terminal and a negative terminal.

Cavity: As used in this disclosure, a cavity is an empty space or negative space that is formed within an object.

Diode: As used in this disclosure, a diode is a two terminal semiconductor device that allows current flow in only one direction. The two terminals are called the anode and the cathode. Electric current is allowed to pass from the anode to the cathode.

Electromagnetic Radiation: As used in this disclosure, electromagnetic radiation refers to an interaction between electric fields and magnetic fields that is capable of transmitting energy through a vacuum.

Field of Illumination: As used in this disclosure, a field of illumination refers to an area illuminated by electromagnetic radiation projected from an electrical device such as a lamp or transmission antenna.

Form Factor: As used in this disclosure, the term form factor refers to the size and shape of an object.

Illumination: As used in this disclosure, light refers to electromagnetic radiation contained with an area. Illumination is a synonym for light, particularly in cases where a measure of the amount of visible electromagnetic radiation in a space is called for.

Impact: As used in this disclosure, an impact refers to an exchange of momentum between two objects over a duration. An impact often refers to a collision between two objects.

Lamp: As used in this disclosure, a lamp is an electrical device that generates (typically visible spectrum) electromagnetic radiation.

Lantern: As used in this disclosure, a lantern is a lamp with a self-contained power source that allows the lantern to illuminate a space without drawing energy from an external power source.

LED: As used in this disclosure, an LED is an acronym for a light emitting diode. A light emitting diode is a diode that is also a light source.

Logical Device: As used in this disclosure, a logical device is a programmable electrical device that processes externally provided inputs to generate outputs that are determined from a previously programmed set of instructions.

Negative Space: As used in this disclosure, negative space is a method of defining an object through the use of open or empty space as the definition of the object itself, or, through the use of open or empty space to describe the boundaries of an object.

Pan: As used in this disclosure, a pan is a hollow and prism-shaped containment structure. The pan has a single open face. The open face of the pan is often, but not always, the superior face of the pan. The open face is a surface selected from the group consisting of: a) an end of the prism structure that forms the pan; and, b) a lateral face of the prism structure that forms the pan. A semi-enclosed pan refers to a pan wherein an end of prism structure of the pan and a portion of the lateral face of the pan is also open.

PDD: As used in this disclosure, PDD is an acronym for personal data device.

Personal Data Device: As used in this disclosure, a personal data device is a handheld logical device that is used for managing personal information and communication. Examples of personal data device include, but are not limited to, cellular phones, tablets, and smartphones.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Rigid Structure: As used in this disclosure, a rigid structure is a solid structure formed from an inelastic material that resists changes in shape. A rigid structure will permanently deform as it fails under a force.

Sacrificial Structure: As used in this disclosure, a sacrificial structure is a first object or structure that protects a second object or structure from damage. More specifically, the sacrificial structure protects the second object or structure by being damaged instead of the second object or structure.

Shell: As used in this disclosure, a shell is a structure that forms an outer covering intended to contain an object. Shells are often, but not necessarily, rigid or semi-rigid structures that are intended to protect the object contained within it.

Spectrum: As used in this disclosure, a spectrum refers to the distribution and amplitude of the component frequencies of a source of electromagnetic radiation. Spectrums are typically organized and displayed by frequency or frequency range.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Transistor: As used in this disclosure, a transistor is a general term for a three terminal semiconducting electrical device that is used for electrical signal amplification and electrical switching applications. There are several designs of transistors. A common example of a transistor is an NPN transistor that further comprises a collector terminal, an emitter terminal, and a base terminal and which consists of a combination of two rectifying junctions (a diode is an example of a rectifying junction). Current flowing from the collector terminal through the emitter terminal crosses the two rectifier junctions. The amount of the electric current crossing the two rectified junctions is controlled by the amount of electric current that flows through the base terminal. This disclosure assumes the use of an NPN transistor. This assumption is made solely for the purposes of simplicity and clarity of exposition. Those skilled in the electrical arts will recognize that other types of transistors, including but not limited to, field effect transistors and PNP transistors, can be substituted for an NPN transistor without undue experimentation.

Ultraviolet Light: As used in this disclosure, ultraviolet light is understood to be electromagnetic radiation with a wavelength lesser than visible light. In general usage, ultraviolet light is taken to mean electromagnetic radiation with a wavelength less than 400 nm.

UV: As used in this disclosure, UV is an abbreviation for ultraviolet.

With respect to the above description, it is to be realized that the optimum dimensional relationship for the various components of the invention described above and in FIGS.

1 through 8 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A smartphone case with integrated UV lights comprising
    a PDD shell, a personal data device, and a UV lamp circuit;
    wherein the smartphone case with integrated UV lights is a lantern;
    wherein the PDD shell contains the personal data device and the UV lamp circuit;
    wherein the personal data device forms an electrical connection with the UV lamp circuit;
    wherein the personal data device provides electrical power to the UV lamp circuit;
    wherein the personal data device controls the operation of the UV lamp circuit;
    wherein the UV lamp circuit generates an illumination of electromagnetic radiation in the ultraviolet spectrum;
    wherein the field of illumination of electromagnetic radiation in the ultraviolet spectrum generated by the smartphone case with integrated UV light detects biological material that is not otherwise illuminated by electromagnetic radiation in the visible spectrum.

2. The smartphone case with integrated UV lights according to claim 1
    wherein the PDD shell is a rigid structure;
    wherein the PDD shell is a protective structure;
    wherein the PDD shell is formed as a pan;
    wherein the PDD shell contains the personal data device such that the personal data device can be used while contained in the PDD shell.

3. The smartphone case with integrated UV lights according to claim 2
    wherein the PDD shell is a sacrificial structure that protects the personal data device from impact damage;
    wherein the PDD shell contains the UV lamp circuit such that the field of illumination generated by the UV lamp circuit is targeted in a direction away from the personal data device.

4. The smartphone case with integrated UV lights according to claim 3 wherein the personal data device is a programmable electrical device that provides data management and communication services.

5. The smartphone case with integrated UV lights according to claim 4
    wherein the UV lamp circuit is an electric circuit;
    wherein the UV lamp circuit electrically connects to the personal data device;
    wherein the personal data device powers the operation of the UV lamp circuit;
    wherein the personal data device controls the operation of the UV lamp circuit.

6. The smartphone case with integrated UV lights according to claim 5
    wherein the PDD shell comprises a PDD pan and one or more lamp cavities;
    wherein each of the one or more lamp cavities is a negative space that is formed in the PDD pan of the PDD shell.

7. The smartphone case with integrated UV lights according to claim 6
    wherein the personal data device further comprises a battery, an application, and a transistor;
    wherein the battery is an electrochemical device;
    wherein the transistor is a three-terminal semiconductor device;
    wherein the application is a set of logical operating instructions that are performed by the personal data device.

8. The smartphone case with integrated UV lights according to claim 7 wherein the UV lamp circuit electrically connects in series with the transistor of the personal data device.

9. The smartphone case with integrated UV lights according to claim 8
    wherein the UV lamp circuit is selected from the group consisting of one or more UV bulbs and a LED circuit;
    wherein each of the one or more UV bulbs is a light bulb;
    wherein the LED circuit generates an ultraviolet illumination;
    wherein the LED circuit is electrically powered;
    wherein the LED circuit is wired in series between the transistor and the battery.

10. The smartphone case with integrated UV lights according to claim 9
    wherein the PDD pan is a rigid structure;
    wherein the PDD pan is a pan shaped structure;
    wherein the PDD pan is a disk structure;
    wherein the PDD pan is sized to receive the personal data device.

11. The smartphone case with integrated UV lights according to claim 10
    wherein the PDD pan is a sacrificial structure;
    wherein the PDD pan forms a protective shell around the personal data device that protects the personal data device from impact damage.

12. The smartphone case with integrated UV lights according to claim 11 wherein the PDD pan contains the UV lamp circuit.

13. The smartphone case with integrated UV lights according to claim 12
    wherein the PDD pan further comprises an open face and a closed face;
    wherein the open face is the open surface of the pan structure of the PDD pan;
    wherein the open face forms a congruent end of the disk structure of the disk structure of the PDD pan;
    wherein the closed face is a congruent end of the disk structure of the disk structure of the PDD pan;
    wherein the closed face is the face of the PDD pan that is distal from the open face;
    wherein the closed face forms a solid surface that protects the personal data device from impact damage.

14. The smartphone case with integrated UV lights according to claim 13
    wherein each of the one or more lamp cavities is a negative space that is formed in the closed face of the pan structure of the PDD pan of the PDD shell;
    wherein the UV lamp circuit mounts in the one or more lamp cavities such that the UV lamp circuit projects a field of ultraviolet illumination that projects away from the closed face of the PDD pan in a direction away from the personal data device.

15. The smartphone case with integrated UV lights according to claim 14 wherein the battery converts chemical potential energy into the electrical energy used to power the personal data device and the UV lamp circuit.

16. The smartphone case with integrated UV lights according to claim 15
   wherein the personal data device controls the operation of the UV lamp circuit;
   wherein the application forms an interface used to control the operation of the UV lamp circuit;
   wherein the application receives instruction through the user interface of the personal data device to illuminate the UV lamp circuit;
   wherein the application instructs the personal data device to apply a voltage to the base of the transistor such that electricity will flow from the battery to the UV lamp circuit to illuminate the UV lamp circuit;
   wherein the application further receives and transmits instructions to extinguish the UV lamp circuit to the personal data device.

17. The smartphone case with integrated UV lights according to claim 16
   wherein each of the one or more UV bulbs generates an ultraviolet illumination;
   wherein each of the one or more UV bulbs is electrically powered;
   wherein each of the one or more UV bulbs is wired in series between the transistor and the battery.

18. The smartphone case with integrated UV lights according to claim 17
   wherein the LED circuit further comprises one or more LEDs and a limit resistor;
   wherein each of the one or more LEDs is a two terminal semiconductor device;
   wherein each of the one or more LEDs generates electromagnetic radiation when electricity passes through the any selected LED;
   wherein each of the one or more LEDs is selected such that each of the one or more LEDs generates electromagnetic radiation in the ultraviolet spectrum;
   wherein each of the one or more LEDs mounts in the one or more lamp cavities such that the electromagnetic radiation generated by the one or more LEDs creates the previously described field of illumination.

19. The smartphone case with integrated UV lights according to claim 18
   wherein the limit resistor connects in series between the transistor of the personal data device and each of the one or more LEDs;
   wherein the limit resistor limits the flow of electricity through each of the one or more LEDs.

20. The smartphone case with integrated UV lights according to claim 19
   wherein each of the one or more LEDs are wired in parallel across from each other;
   wherein each of the one or more UV bulbs are wired in parallel to each other.

* * * * *